United States Patent [19]

Oh et al.

[11] Patent Number: 5,198,582
[45] Date of Patent: * Mar. 30, 1993

[54] PROCESS FOR PREPARING SYMMETRIC N,N'-DISUBSTITUTED AROMATIC UREA

[75] Inventors: Jae S. Oh; Sang M. Lee, both of Daejeon, Rep. of Korea

[73] Assignee: Lucky Ltd., Seoul, Rep. of Korea

[*] Notice: The portion of the term of this patent subsequent to Feb. 25, 2009 has been disclaimed.

[21] Appl. No.: 780,197

[22] Filed: Oct. 22, 1991

Related U.S. Application Data

[63] Continuation-in-part of Ser. No. 606,721, Oct. 31, 1990, Pat. No. 5,091,571.

[51] Int. Cl.$^5$ .................. C07C 275/28; C07C 275/30
[52] U.S. Cl. ........................................ 564/52; 564/47; 564/48; 564/53; 564/54; 564/55
[58] Field of Search ................. 564/52, 48, 47, 53, 564/55, 54

[56] References Cited

U.S. PATENT DOCUMENTS

| | | | |
|---|---|---|---|
| 4,052,454 | 10/1977 | Zajacek et al. | 260/553 |
| 4,603,216 | 7/1986 | Grate et al. | 560/24 |
| 5,091,571 | 2/1992 | Lee et al. | 564/52 |

FOREIGN PATENT DOCUMENTS 319111A 6/1989 European Pat. Off. .............. 564/52

OTHER PUBLICATIONS

Oh et al. Ind. Eng. Chem. Res. 1991, 30, 1456-1461.
Fukuoka et al., Chem Tech Nov. 1984, 670-676.
Franz et al. J. Org Chem, vol. 26, 3309, 1961.
Dieck et al, J. Org. Chem., vol. 40, No. 19, 1975, 2819-2822.
Matthys et al., Inorganic Chemistry, vol. 9, No. 2, Feb. 1970, 342-345.

*Primary Examiner*—Richard L. Raymond
*Assistant Examiner*—Shailendra Kumar
*Attorney, Agent, or Firm*—Birch, Stewart, Kolasch & Birch

[57] ABSTRACT

A process for preparing N,N'-disubstituted urea derivatives of the following formula (I)

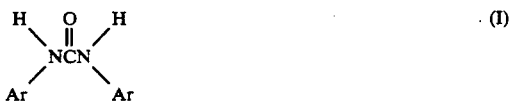

wherein Ar represents an unsubstituted aromatic radical or an aromatic radical substituted with a halogen atom, an alkyl group, or an alkoxy group, which comprises reacting an aromatic mono-nitro compound, an aromatic primary amine, and synthesis gas in the presence of a catalyst consisting essentially of a divalent palladium compound as a main catalyst component and an ammonium or a phosphonium salt containing halogen atom as a co-catalyst component, and a non-polar solvent.

11 Claims, 1 Drawing Sheet

PROCESS FOR PREPARING SYMMETRIC N,N'-DISUBSTITUTED AROMATIC UREA

CROSS-REFERENCE TO RELATED APPLICATION

This is a continuation-in-part application of U.S. patent application, Ser. No. 07/606,721, filed on Oct. 31, 1990, now U.S. Pat. No. 509,157,1, which is fully incorporated herein by reference.

BACKGROUND OF THE INVENTION

1. Field of the Invention

The present invention relates to a process for preparing N,N'-disubstituted urea and more particularly, to an improved process for preparing N,N'-disubstituted urea derivatives of the following formula (I)

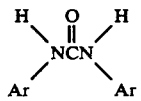

wherein Ar represents an unsubstituted aromatic radical or an aromatic radical substituted with a halogen atom, an alkyl group, or an alkoxy group, which comprises reacting an aromatic mono-nitro compound, an aromatic primary amine, and synthesis gas in the presence of a catalyst consisting essentially of a divalent palladium compound as a main catalyst component and an ammonium or a phosphonium salt containing halogen atom as a co-catalyst component, and a non-polar solvent.

2. Description of the Prior Art

The conventional N,N'-disubstituted urea is an important intermediate for the production of carbamates which are raw materials for agrochemicals. The conventional methods for preparing N,N'-disubstituted urea have heretofore been developed by reaction of amines with carbon monoxide in the presence of non-metal catalysts such as tertiary aliphatic amine (*J. Org. Chem.*, 26, 3309, 1961), selenium (*J. Am. Chem. Soc.*, 93, 6344, 1971), and metal catalysts such as cobalt carbonyl (*Can. J. Chem.*, 40, 1718, 1962), and silver acetate (*J. Org. Chem.*, 37, 2670, 1972).

The disclosure in *J. Org. Chem.*, 26, 3309, 1961 relates to a method to synthesize ureas using tertiary aliphatic amine as a catalyst, but the yield of urea is 86.2% only when an excess amount of sulfur is reacted with amine and carbon monoxide. The use of sulfur produces unwanted by-product hydrogen sulfide and its treatment imposes additional cost to the process economy.

A method of the preparation of ureas as by synthesizing ureas from aliphatic amines, carbon monoxide, and oxygen using selenium as a catalyst is disclosed in *J. Am. Chem. Soc.*, 93, 6344, 1971. The selenium catalyst has a well-known toxicity problem. A continuous flow of oxygen is also required in the method to precipitate the selenium catalyst, which is not only dangerous due to the explosion but also expensive. Those methods using catalysts such as sulfur, selenium, etc., have high yield and selectivity. However, it is very difficult to separate and recover those catalysts. That is, unless the catalysts can be separated for reuse, the catalyst loss generally tends to make the expense of using the process prohibitive for economic purpose.

U.S. Pat. No. 4,052,454 also discloses a process for the production of ureas by synthesizing disubstituted urea with a selenium or sulfur catalyst. The maximum yield of the disclosure using the selenium catalyst is limited to 67.3%. For the sulfur compound, which is the catalyst actually claimed in the disclosure, the urea yield given in the example is merely 3.4-7.7%, and it is clearly impractical. The disclosure suggests to use more amine in moles than nitro compound. However, this method is limited to the preparation of unsymmetric urea. For the preparation of symmetric urea, the use of water is proposed.

Other methods for preparing N,N'-disubstituted urea in the presence of metal catalysts except platinum group catalysts are not practical since the yield and selectivity of the reaction is quite low.

The processes using platinum group catalysts are disclosed in European Patent Publication No. 319,111, Japanese Patent Publication No. 53-41,123, Japanese Patent Laid-Open Publication Nos. 58-144,363 and 62-59,253, and *J. Org. Chem. Vol.* 40 (19), 2819, 1975.

Among such disclosures, European Patent Publication No. 319,111 uses a salt of Cu, Fe, Mn, V, Cr, Zn, Sn, U, or Ce in addition to a palladium compound. It is well known that these salts promote the reaction called the Wacker-type chemistry, which involves a redox cycle between Pd(II) and Pd(O) with a metal salt serving as a reoxidant of Pd(O) to active Pd(II) species. Hence, the presence of a reoxidant is a necessity in this type of reaction. Otherwise, the catalyst is separated as a zero-valent metal, and the efficiency of the reaction decreases. When an excess amount of amine is used, unsymmetric urea is mainly obtained by this method. The best example given in this disclosure is 73% yield of 1,1-dimethyl-3(4-chlorobenzene)-urea for 20 hours of reaction time.

Japanese Patent Publication No. 53-41,123 and Japanese Patent Laid-Open Publication No. 58-144,365 relate to a process for preparing N,N'-disubstituted urea by reaction of amines with carbon monoxide under an elevated temperature and a high pressure. In such prior art methods, it is not only difficult to control the partial pressure of two kinds of gases involved, i.e. carbon monoxide and oxygen, but also there is a danger of explosion due to the oxygen.

A method disclosed in J. Org. Chem. Vol. 40 (19), 2819, 1975, describes a method of synthesizing N,N'-diaryl urea at 1 atm, 90° C. with the initial amine/nitro compound molar ratio less than 1. In this disclosure, tri-n-butyl amine is used up to 50% together with solvent to maintain the catalyst activity. Otherwise, the activity of the catalyst is suddenly decreased during the reaction. Since a small amount of aromatic primary amine is employed, the decomposition of catalyst is not effectively inhibited. Hence, the catalyst cannot be reused and recycled, and the activity of the catalyst is reduced to 50% of the initial activity after one cycle of the reaction. Although it is ideal for this reaction to dissolve the palladium catalyst completely in the aromatic primary amine, it is actually very difficult to achieve due to the low amine concentration in the reaction mixture. Furthermore, the reaction pressure is too low to conduct an efficient carbonylation reaction. As a result, the yield of the aromatic urea according to the method is as low as 64%.

The process disclosed in Japanese Patent Laid-Open Publication No. 62-59,253 gives relatively high yield and selectivity. However, it requires expensive catalysts such as rhodium and ruthenium compounds. Furthermore, the appearance of the resulting N,N'-disubstituted urea is not neat, and the catalysts are unstable at a high temperature and decomposed around the reaction temperature.

All the above methods use pure carbon monoxide as a raw material. Since carbon monoxide is usually separated from synthesis gas by cryogenic distillation or solvent absorption, additional investments for the purification of carbon monoxide are required. On the other hand, the synthesis gas itself, consisting of mainly carbon monoxide and hydrogen in various proportions, can be manufactured cheaply by the methods such as coal gasification, partial oxidation or steam cracking of natural gas and oil, etc. When the synthesis gas is used instead of pure carbon monoxide as a raw material for urea synthesis, it will be superior in the economy of the raw material than any other process disclosed so far. Furthermore, when the hydrogen in synthesis gas reacts with a mono-nitro compound producing a corresponding amine during the synthesis reaction of urea such as formula (I), it can reduce the consumption of the amine which is more expensive than the corresponding mono-nitro compound, and the process economy will be greatly improved.

Inorg. Chem., Vol. 9,342, 1970 disclosed a method of N,N'-disubstituted urea synthesis by reacting nitrobenzene with synthesis gas. The method requires high pressure of carbon monoxide and the yield of urea is as low as 54%.

In order to avoid such problems, the present inventors are also prosecuting another U.S. patent application Ser. No. 07/606,721, filed on Oct. 31, 1990, now allowed, which is fully incorporated herein by reference and discloses a process for the preparation of N,N'-disubstituted urea derivatives comprising reacting an aromatic mono-nitro compound, aromatic primary amines, and carbon monoxide in the presence of catalysts. However, it is difficult to separate the carbon monoxide and require a large amount of the aromatic primary amines.

SUMMARY OF THE INVENTION

Accordingly, it is an object of the present invention to provide an improved process for preparing N,N'-disubstituted urea derivatives of the below formula (I) in high yield, which eliminate the above problems encountered in a conventional method.

Another object of the present invention is to provide a process of the preparation of N,N'-disubstituted urea which comprises reacting an aromatic mono-nitro compound and an aromatic primary amine with synthesis gas in the presence of a catalyst composition consisting of a palladium compound as a main catalyst and an ammonium or phosphonium salt as a co-catalyst wherein the molar ratio of the aromatic primary amine to the mono-nitro compound in the reaction mixture is greater than two so as to attain the high yield of the desired product, inhibit the catalyst decomposition during the reaction, and recover the catalyst maintaining the initial activity without any further treatment.

A further object of the present invention is to provide a process of the preparation of N,N'-disubstituted urea derivatives which comprise reacting an aromatic primary amine, an aromatic mono-nitro compound, and synthesis gas in the presence of a catalyst composition wherein the hydrogen to carbon monoxide molar ratio of the synthesis gas is less than 5, the aromatic primary amine is used both as a reactant and as a solvent so as to wash the product solids for the complete recovery of the catalyst, the reaction temperature is between 50° and 200° C. and the reaction pressure is between 5 and 100 atm.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention relates to an improved process for preparing N,N'-disubstituted urea derivatives of the following formula (I)

wherein Ar represents an unsubstituted aromatic radical or an aromatic radical substituted with a halogen atom, an alkyl group, or an alkoxy group, which comprises reacting an aromatic mono-nitro compound, an aromatic primary amine, and synthesis gas in the presence of a catalyst consisting essentially of a divalent palladium compound as a main catalyst component and an ammonium or a phosphonium salt containing halogen atom as a co-catalyst component, and a non-polar solvent.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF THE PREFERRED EMBODIMENTS

Figure 1:
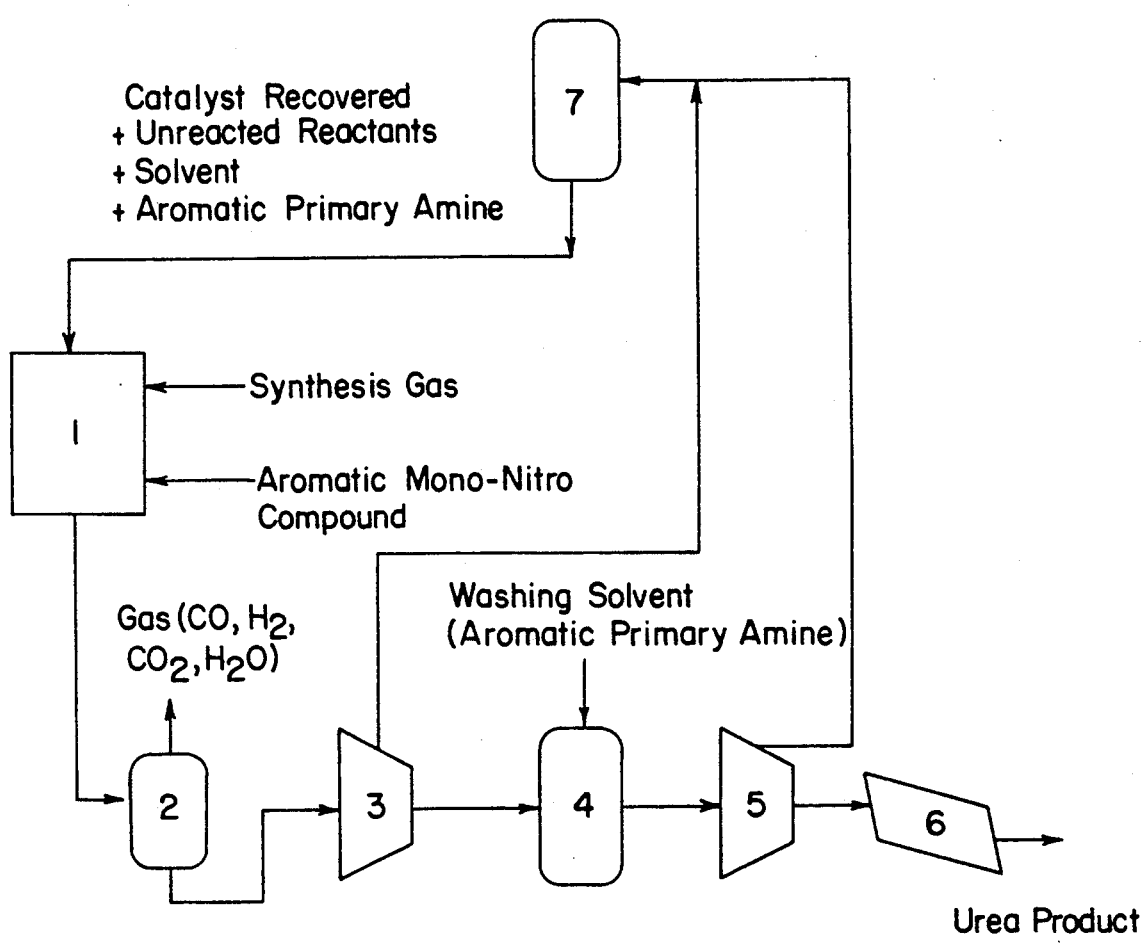
FIG. 1 shows a schematic diagram of the continuous process of the present invention for preparing N,N'-disubstituted urea. The process can be either batch or continuous mode.

Referring now in detail to the drawings for the purpose of illustrating preferred embodiments of the present invention, the process of the preparation of N,N'-disubstituted urea as shown in FIG. 1, comprises reacting an aromatic mono-nitro compound, an aromatic primary amine, and synthesis gas in the presence of a catalyst composition consisting of a palladium compound as a main catalyst and an ammonium or phosphonium salt containing halogen atom as a co-catalyst, and a non-polar solvent.

The aromatic mono-nitro compound is selected from the group consisting of nitrobenzenes, nitronaphthalenes, nitroanthracenes, and nitrobiphenyls. They include, for example, nitrobenzene, o-, m-, or p-nitrotoluene, o-nitro-p-xylene, 2-methyl-1-nitronaphthalene, o-, m- or p-chloronitrobenzene, 1-bromo-4-nitrobenzene, 2-chloro-6-nitrotoluene, 4-chloro-3-nitrotoluene, 1,4-dichloro-2-nitrobenzene, 3,4-dichloro-1-nitrobenzene, alphachloro-m-nitrotoluene, 1,2,4-trichloro-5-nitrobenzene, etc.

The aromatic primary amine, which corresponds to the aromatic mono-nitro compound, is selected from the group consisting of anilines, aminoanthracenes, aminoanthracenes, and aminobiphenyls. They include aniline, o-, m-, or p-toluidine, o-, m-, p-chloroaniline, alpha- or beta-naphthylamine, 2-methyl-1-aminoaphthalene, aminotoluene, etc.

Since the primary amine used in the present invention functions not only as a reactant but also as a solvent, it is preferred to use it greater than two in moles than the mono-nitro compound so that it inhibits the decomposition of the catalyst and makes it easy to recover the catalyst by washing the product solids with the primary amine.

The reaction for the production of N,N'-disubstituted urea given in the formula (I) proceeds competitively as shown in the following reaction schemes (1) and (2):

$$ArNH_2 + ArNO_2 + 3CO \rightarrow ArNHCNHAr + 2CO_2 \quad (1)$$

$$5ArNH_2 + ArNO_2 + 3CO \rightarrow 3ArNHCNHAr + 2H_2O \quad (2)$$

wherein Ar is the same as defined above.

The production rate of N,N'-disubstituted urea depends on the molar ratio of the aromatic mono-nitro compound to the aromatic primary amine. As shown in the above equations (1) and (2), when the amount of mono-nitro compound is constant, the larger the amount of aromatic primary amine, the larger the amount of N,N'-disubstituted urea is produced. It is because the reaction rate of the equation (2) is increased more rapidly than the reaction rate of the equation (1) when the concentration of the aromatic primary amine increases.

The synthesis gas used in the present invention does not have any particular limitation in source or manufacturing process. It is sufficient to purify the synthesis gas by a general procedure to remove such components as sulfur compound, carbon dioxide, ammonia, etc., which can be poisonous to the catalyst. Especially, there is no need to remove nitrogen in the synthesis gas since nitrogen is not involved in the reaction.

The hydrogen to carbon monoxide molar ratio of the synthesis gas used in the present invention is less than 5, and preferably less than 2.

When the synthesis gas is used instead of carbon monoxide in the synthesis of N,N'-disubstituted urea, a portion of mono-nitro compound reacts with hydrogen producing a corresponding amine as shown in the following reaction scheme (3):

$$ArNO_2 + 2CO + H_2 \rightarrow ArNH_2 + 2CO_2 \quad (3)$$

wherein Ar is the same as defined above. Therefore, the consumption of the aromatic mon-nitro compound is reduced by the reaction (3) and the process economy is improved by utilizing cheap synthesis gas.

The palladium compounds useful as a main catalyst in this invention are composed of a divalent palladium ion. The can be represented by the following formula (II)

$$PdX_2L_2 \quad (II)$$

wherein X indicates halogen atom, $NO_3$, $OCOCH_3$, $OCOCF_3$, and L indicated $PR_3$ (R is methyl, ethyl, propyl, butyl, or phenyl), $C_6H_5NH_2$, $CH_3CN$, p-$ClC_6H_5NH_2$, and p-$CH_3C_6H_4NH_2$ as a ligand. The amount of the main catalyst is preferably between 1/3000 and 1/10 mole per mole of the aromatic mono-nitro compound. When the main catalyst of the type PdX, is used, it is necessary to add the aforementioned ligands to the reaction mixture. The amount of the ligand is preferably more than 2 moles per mole of the main catalyst.

The halogen-containing compound used as the co-catalyst is ammonium salts of the formula $[R'_4N^+]X'^-$ and phosphonium salts of the formula $[R'_4P^+]X'^-$, wherein R' represents hydrogen atom, paraffinic, aromatic, or paraffinic aromatic group, and X' represents halogen atom. Such compounds include, for example, ammonium slats such as tetramethyl ammonium chloride, tetraethyl ammonium chloride, tetrapropyl ammonium chloride, tetrabutyl ammonium chloride, tetramethyl ammonium bromide, tetraethyl ammonium bromide, tetrapropyl ammonium bromide, tetrabutyl ammonium bromide, tetramethyl ammonium iodide, tetraethyl ammonium iodide, tetrapropyl ammonium iodide, tetrabutyl ammonium iodide, trimethyl benzyl ammonium chloride, etc., and phosphonium salts such as tetramethyl phosphonium chloride, tetraethyl phosphonium chloride, tetrapropyl phosphonium chloride, tetrabutyl phosphonium chloride, tetramethyl phosphonium bromide, tetraethyl phosphonium bromide, tetrapropyl phosphonium bromide, tetrabutyl phosphonium bromide, tetramethyl phosphonium iodide, tetraethyl phosphonium iodide, tetrapropyl phosphonium iodide, tetrabutyl phosphonium iodide, etc.

The amount of the co-catalyst is between 1 and 20 moles per mole of the main catalyst, i.e. the palladium compound. When the amount of the co-catalyst is less than 1 mole per mole of the main catalyst, the rate of the reaction is negligible. On the other hand, if it is more than 20 moles per mole of the main catalyst, it is not economical.

It is preferable to control the amounts of the main catalyst and the ligand so as to dissolve them completely considering the solubilities of each component under the reaction conditions such as reaction temperature, reaction pressure, amount of the aromatic primary amine, and amount of the solvent.

The process of the invention can be carried out in the absence of a solvent, but the use of a solvent is not precluded. Suitable solvents are preferably non-polar solvents such as benzene, toluene, and xylene, which hardly dissolve N,N'-disubstituted urea.

The reaction temperature is generally held in the range between 50° and 200° C., preferably between 80° and 140° C. When the reaction temperature is lower than the above range, a large amount of mono-nitro compound remains unreacted. Whereas, if the reaction temperature is higher than the above range, the catalyst tends to be deactivated or decomposed.

Even though it is possible to carry out the reaction at any pressure greater than 1 atm., the reaction pressure is generally held in the range between 5 and 100 atm., and preferably between 5 and 40 atm. when the reaction pressure is less than 5 atm., the reaction rate is too slow. When the reaction pressure is more than 100 atm., it requires much expenses for high pressure equipments.

The reaction time depends on the nature and amount of reactants, the reaction pressure, the reaction temperature, the type and the amount of catalyst used. However, it is generally in the range of 10 minutes to 10 hours.

After completion of the reaction, the final product, N,N'-disubstituted urea, is recovered as a solid from the reaction mixture by filtration or centrifugation and washing. Since the main catalyst, co-catalyst, unreacted materials and solvent present in the remaining liquid phase, the main catalyst and co-catalyst are almost perfectly recovered from the mixture by the filtration of product solids. The obtained urea derivatives are subjected to a conventional procedure including washing and separation under reduced or elevated pressure, thereby obtaining the product with high purity. At the same time, the catalyst mixed with the solid product is recovered almost completely.

The aromatic primary amine is preferably used for washing, and more preferably aromatic primary amine which is exactly the same as the reactant, since it can be used for the next reaction without any further treatment.

As shown in FIG. 1, when the present invention is applied to a continuous mode, raw materials are charged into the reactor 1 and reacted. After the reaction is completed, the gases which are mainly carbon monoxide, hydrogen, carbon dioxide, and water vapor, are separated from the reaction mixture by a gas separator 2. In the first centrifugal separator 3, the resulted slurry is separated into solid and liquid materials. The solid material is conveyed to the slurry drum 4 where the solvent for catalyst recovery is charged. The mixture is then thoroughly stirred and separated in the second centrifugal separator 5. The desired N,N'-disubstituted urea is obtained as a solid after drying in the drier 6. The unreacted materials, solvent, main catalyst and co-catalyst from the first and second centrifugal separators 3 and 5 are collected in the receiving drum 7. The liquid in a receiving drum 7 is recharged into the reactor 1.

Thus the characteristics of the present invention are to use a sufficient amount of aromatic primary amine which is enough to dissolve catalysts to maintain a reaction pressure which is optimal for the reaction and catalyst activity, and to use the same aromatic primary amine both as a reactant and as a solvent for catalyst recovery, thereby improving the yield and purity of the desired product remarkably and reusing the catalyst without loss by simple filtration and washing of the product solids.

The present invention will now be described in more detail in connection with the following examples which should be considered as being exemplary and not limiting the present invention.

In all of these examples, the reaction was carried out by batch mode in an electromagnetically stirring type autoclave made of Hastelloy C having a capacity of 300 ml. Reactants are heated by a heater attached to the outside of the reactor. After the reaction was completed, the reaction mixture was cooled down to room temperature by a cooling coil installed at the inside of the reactor. The reaction products were analyzed by gas chromatography and high performance liquid chromatography (HPLC). In the gas chromatographic analyses, t-butyl benzene was used as an internal standard.

The yield of N,N'-disubstituted urea was calculated by the following equation:

$$\text{YIELD (\%)} = \frac{2(\text{moles of N,N'-disubstituted urea product})}{\text{reacted moles of aromatic mono-nitro compound and aromatic primary amine}}$$

EXAMPLE 1

Into a 300 ml autoclave were charged 6.15 g (50 mmoles) of nitrobenzene, 27.9 g (300 mmoles) of aniline, 0.15 g of palladium acetate, 1 g of triphenyl phosphine, 2 g of tetraethyl ammonium chloride, t-butyl benzene (as an internal standard for gas chromatographic analysis), and 60 g of xylene. The autoclave was initially purged with pressurized synthesis gas at 10 atm., of which the hydrogen to carbon monoxide molar ratio is 0.5, three times, and the synthesis gas pressure of 60 atm. was established at room temperature. The reaction mixture was heated with stirring and held at 120° C. for 2.5 hours. During the reaction, liquid samples were taken through the sampling valve. After completion of the reaction, the reaction mixture was cooled to room temperature and the gas was discharged from the autoclave. After the filtration of the reaction mixture under the reduced pressure, the precipitates were washed with 18.6 g (200 mmoles) of aniline, and 50 g of xylene, and then dried. As a result, 18.5 g of white precipitate was obtained. Analysis of the remaining solution revealed that the conversion of nitrobenzene was 99.1% and the yield of N,N'-dipheynl urea (DPU) was 97.1%.

EXAMPLE 2

The procedure of the Example 1 was repeated except that the reaction was carried out at 40 atm. with the synthesis gas of the hydrogen to carbon monoxide molar ratio 1. The analysis of the product revealed that the conversion of nitrobenzene was 98.8% and the yield of N,N'-diphenyl urea was 97.0%.

EXAMPLE 3

The procedure of the Example 1 was repeated except that the reaction was carried out at 60 atm. with the synthesis gas of the hydrogen to carbon monoxide molar ratio 2. The analysis of the product revealed that the conversion of nitrobenzene was 98.3% and the yield of N,N'-diphenyl urea was 96.8%.

EXAMPLE 4

Reaction A

The procedure of the Example 1 was repeated except that the reaction was carried out at 40 atm. with carbon monoxide instead of synthesis gas for 1.5 hours. After the filtration of the reaction mixture under the reduced pressure (Supernatant A), the precipitates were washed with 18.6 g (200 mmoles) of aniline (Supernatant B), and 50 g of xylene, and then dried. As a result 18.4 g of white precipitate was obtained. Analysis of the remaining solution revealed that the conversion of nitrobenzene was 100% and the yield of N,N'-diphenyl urea (DPU) was 97.3%. The analysis by the inductively coupled plasma (ICP) indicated that the palladium component of the catalyst did not present in the product solids. In other words, all the catalyst existed in the filtrate.

Reaction B

Into a 300 ml autoclave were charged the Supernatants A and B obtained from the Reaction A and 6.15 g (50 mmoles) of nitrobenzene. Then the procedure of the Reaction A was repeated. After the filtration of the reaction mixture (Supernatant C), the precipitate was washed with 18.6 g of aniline (200 mmoles), filtered again (Supernatant D), washed again with 50 g of xylene, and dried. As a result, 18.5 g of white precipitate was obtained. Analysis of the remaining solution revealed that the conversion of nitrobenzene was 100% and the yield of DPU was 98.0%, which indicates no decrease in the catalyst activity.

Reaction C

Into a 300 ml autoclave were charged the Supernatants C and D obtained from the Reaction B and 6.15 g (50 mmoles) of nitrobenzene. Then the procedure of the Reaction A was repeated. After the filtration of the reaction mixture (Supernatant E), the precipitate was washed with 18.6 g of aniline (200 mmoles), filtered again (Supernatant F), washed again with 50 g of xylene, and dried. Analysis of the remaining solution revealed that the conversion of nitrobenzene was 100% and the yield of DPU was 98.0%. The analysis by ICP indicated that the palladium component of the catalyst did not present in the product solids.

Reaction D

Into a 300 ml autoclave were charged the Supernatants E and F obtained from the Reaction C and 6.15 g (50 mmoles) of nitrobenzene. Then the procedure of the Reaction A was repeated. As a result, 18.5 g of white precipitate was obtained. Analysis of the remaining solution revealed that the conversion of nitrobenzene was 100% and the yield of DPU was 98.0%. The ICP analysis showed that no palladium component present in the product solids.

EXAMPLE 5

The procedure of the Reaction A of the Example 4 was repeated except that the xylene was replaced with 60 g of toluene and that the reaction was carried out at 53 atm. and 100° C. for 6 hours. The analysis of the remaining solution revealed that the conversion of nitrobenzene was 95.2% and the yield of N,N'-diphenyl urea was 92.4%.

EXAMPLE 6

The procedure of the Reaction A of the Example 4 was repeated except that tetraethyl ammonium chloride (Et$_4$NCl) was replaced with tetrabutyl phosphonium bromide (Bu$_4$PBr) and that the reaction was carried out for 4 hours. After the reaction, the product mixture was filtered (Supernatant G), and the precipitate was washed with 18.6 g of aniline (200 mmoles), filtered again (Supernatant H), washed with 50 g of xylene, and dried. Analysis of the remaining solution revealed that the conversion of nitrobenzene was 97.8% and the yield of DPU was 96.4%. The ICP analysis showed that no palladium component present in the product solids.

Reaction B

Into a 300 ml autoclave were charged the Supernatants G and H obtained from the Reaction A and 6.15 g (50 mmoles) of nitrobenzene. Then the procedure of the Reaction A was repeated. The conversion of nitrobenzene was 98.4% and the yield of DPU was 97.1%.

EXAMPLE 7

Reaction A

The procedure of the Reaction A of the Example 4 was repeated except that palladium acetate (Pd(CH$_3$COO)$_2$) was replaced with palladium chloride (PdCl$_2$) and that the reaction was carried out for 6 hours. After the reaction, the product mixture was filtered (Supernatant I), and the precipitate was washed with 18.6 g of aniline (200 mmoles), filtered again (Supernatant J), washed again with 50 g of xylene, and dried. Analysis of the remaining solution revealed that the conversion of nitrobenzene was 88.9% and the yield of DPU was 86.1%. The ICP analysis showed that no palladium component present in the product solids.

Reaction B'

Into a 300 ml autoclave were charged the Supernatants I and J obtained from the Reaction A and 6.15 g (50 mmoles) of nitrobenzene. Then the procedure of the Reaction A was repeated. The conversion of nitrobenzene was 98.4% and the yield of DPU was 7.1%.

EXAMPLE 8

Reaction A

The procedure of the Reaction A of the Example 4 was repeated except that palladium acetate (Pd(CH$_3$COO)$_2$) was replaced with palladium trifluoroacetate (Pd(CF$_3$COO)$_2$) and that the reaction was carried out at 62 atm. and 100° C. for 7 hours. After the reaction, the product mixture was filtered (Supernatant K), and the precipitate was washed with 18.6 g of aniline (200 mmoles), filtered again (Supernatant L), washed with 50 g of xylene, and dried. Analysis of the remaining solution revealed that the conversion of nitrobenzene was 96.2% and the yield of DPU was 93.4%. The ICP analysis shoed that no palladium component present in the product solids.

Reaction B

Into a 300 ml autoclave were charged the Supernatants K and L obtained from the Reaction A and 6.15 g (50 mmoles) of nitrobenzene. Then the procedure of the Reaction A was repeated. The conversion of nitrobenzene was 97.0% and the yield of DPU was 94.0%.

COMPARATIVE EXAMPLE 1

The procedure of the Reaction A of the Example 4 was repeated except that aniline was omitted. Aniline was not formed and the reaction did not occur.

COMPARATIVE EXAMPLE 2

The procedure of the Reaction A of the Example 4 was repeated except that nitrobenzene was omitted. The reaction did not occur.

COMPARATIVE EXAMPLE 3

The procedure of the Reaction A of the Example 4 was repeated except that tetraethyl ammonium chloride (Et$_4$NCl) was omitted. The conversion of nitrobenzene was 11.4% and the yield of DPU was 11.5%.

COMPARATIVE EXAMPLE 4

The procedure of the Reaction A of the Example 4 was repeated except that palladium acetate (Pd(CH$_3$COO)$_2$) was replaced with 0.15 g of palladium metal and the reaction was carried out at 50 atm. and 100° C. for 4.5 hours. The reaction did not occur.

COMPARATIVE EXAMPLE 5

The procedure of the Reaction A of the Example 4 was repeated except that tetraethyl ammonium chloride (Et$_4$NCl) was replaced with 2 g of potassium chloride (KCl). The conversion of 55 1%.

COMPARATIVE EXAMPLE 6

The procedure of the Reaction A of the Example 4 was repeated except that tetraethyl ammonium chloride (ET₄NCl) was replaced with 2 g of cupric chloride (CuCl₂) and the reaction was carried out at 55 atm. for 5 hours. The reaction did not occur.

COMPARATIVE EXAMPLE 6

The procedure of the Reaction A of the Example 1 was repeated except that xylene was replaced with 70 ml of acetone. The conversion of nitrobenzene was 25.4% and the yield of N,N'-diphenyl urea was 25.1%.

COMPARATIVE EXAMPLE 8

Reaction A

Into a 300 ml autoclave were charged 6.15 g (50 mmoles) of nitrobenzene, 9.3 g (100 mmoles) of aniline, 0.5 g of palladium acetate, 1 g of triphenyl phosphine, 2 g of tetraethyl ammonium chloride, 5 g of tri-n-butyl amine, t-butyl benzene (as an internal standard for gas chromatographic analysis), and 60 g of xylene. The procedure of the Reaction A of the Example 4 was repeated except that the reaction was carried out at 100° C. for 6 hours. After the reaction, the reaction mixture was filtered under the reduced pressure (Supernatant M), washed with 50 g of xylene, and then dried. Analysis of the remaining solution revealed that the conversion of nitrobenzene was 92.0% and the yield of DPU was 90.0%.

Reaction B

Into a 300 ml autoclave were charged the Supernatant M obtained from the Reaction A, 6.15 g (50 mmoles) of nitrobenzene, and 9.3 g (100 mmoles) of aniline. Then the procedure of the Reaction A was repeated. The conversion of nitrobenzene was 28.0% and the yield of DPU was 26.0%.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A process for preparing N,N'-disubstituted urea of the following formula (I):

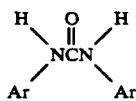

(I)

wherein Ar represents an unsubstituted aromatic radical or an aromatic radical substituted with a halogen atom, an alkyl group or an alkoxy group, which comprises reacting an aromatic mono-nitro compound, an aromatic primary amine, and synthesis gas of carbon monoxide and hydrogen gas mixture in the presence of a catalyst consisting essentially of a divalent palladium compound as a main catalyst component and an ammonium or a phosphonium salt containing halogen atom as a co-catalyst component, and a non-polar solvent.

2. The process of claim 1, wherein said reaction is constructed at a temperature between 50° and 200° C.

3. The process of claim 1, wherein said reaction is constructed at a pressure between 5 and 100 atm.

4. The process of claim 1, wherein said aromatic primary amine is added to the reaction system in an amount equal to or more than 2 moles per mole of the aromatic mono-nitro compound.

5. The process of claim 1, wherein said synthesis gas has a hydrogen to carbon monoxide molar ratio less than 5.

6. The process of claim 1, wherein said palladium compound is represented by PdX₂L₂ wherein X indicates halogen atom, NO₃, OCOCH₃, OCOCF₃, and L indicated PR₃ (R is methyl, ethyl, propyl, butyl, or phenyl), C₆H₅NH₂, CH₃CN, p-ClC₆H₅NH₂, and p-CH₃C₆H₄NH₂ as a ligand.

7. The process of claim 1, wherein said co-catalyst is added to the reaction system in an amount between 1 and 20 moles per mole of palladium compound.

8. The process of claim wherein said halogen atom containing ammonium salt is selected from the group consisting of tetramethyl ammonium chloride, tetraethyl ammonium chloride, tetrapropyl ammonium chloride, tetrabutyl ammonium chloride, tetramethyl ammonium bromide, tetraethyl ammonium bromide, tetrapropyl ammonium bromide, tetrabutyl ammonium bromide, tetramethyl ammonium iodide, tetraethyl ammonium iodide, tetrapropyl ammonium iodide, and tetrabutyl ammonium iodide.

9. The process of claim 1, wherein said halogen atom containing phosphonium salt is selected from the group consisting of tetramethyl phosphonium chloride, tetraethyl phosphonium chloride, tetrapropyl phosphonium chloride, tetrabutyl phosphonium chloride, tetramethyl phosphonium bromide, tetraethyl phosphonium bromide, tetrapropyl phosphonium bromide, tetrabutyl phosphonium bromide, tetramethyl phosphonium iodide, tetraethyl phosphonium iodide, tetrapropyl phosphonium iodide, and tetrabutyl phosphonium iodide.

10. The process of claim 1, wherein said non-polar solvent is selected from the group consisting of benzene, toluene, and xylene.

11. The process of claim 1, wherein said main catalyst and said co-catalyst are easily recovered by filtration of the reaction mixture and washing of the filter cake with said aromatic primary amine.

* * * * *